United States Patent
Mestha et al.

(10) Patent No.: US 7,385,704 B2
(45) Date of Patent: Jun. 10, 2008

(54) TWO-DIMENSIONAL SPECTRAL CAMERAS AND METHODS FOR CAPTURING SPECTRAL INFORMATION USING TWO-DIMENSIONAL SPECTRAL CAMERAS

(75) Inventors: Lalit K. Mestha, Fairport, NY (US); Joel A. Kubby, Santa Cruz, CA (US); Yao Rong Wang, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 182 days.

(21) Appl. No.: 11/092,635

(22) Filed: Mar. 30, 2005

(65) Prior Publication Data

US 2006/0221346 A1 Oct. 5, 2006

(51) Int. Cl.
*G01B 9/02* (2006.01)
*G01J 3/45* (2006.01)

(52) U.S. Cl. ........................................ 356/454; 356/519

(58) Field of Classification Search ................ 356/454, 356/451, 469, 402; 340/5.8; 705/27
See application file for complete search history.

(56) References Cited

U.S. PATENT DOCUMENTS

| | | | | |
|---|---|---|---|---|
| 5,142,414 A * | 8/1992 | Koehler | | 359/578 |
| 5,561,523 A * | 10/1996 | Blomberg et al. | | 356/454 |
| 5,646,729 A * | 7/1997 | Koskinen et al. | | 356/454 |
| 5,909,280 A * | 6/1999 | Zavracky | | 356/454 |
| 6,295,130 B1 * | 9/2001 | Sun et al. | | 356/454 |
| 6,608,685 B2 * | 8/2003 | Wood et al. | | 356/519 |
| 6,836,366 B1 * | 12/2004 | Flanders et al. | | 359/578 |
| 7,061,618 B2 * | 6/2006 | Atia et al. | | 356/454 |
| 2002/0075483 A1 * | 6/2002 | Harris et al. | | 356/453 |
| 2003/0136837 A1 * | 7/2003 | Amon et al. | | 235/435 |
| 2004/0078299 A1 * | 4/2004 | Down-Logan et al. | | 705/27 |
| 2004/0218187 A1 * | 11/2004 | Cole | | 356/454 |
| 2005/0030545 A1 * | 2/2005 | Tuschel et al. | | 356/454 |

OTHER PUBLICATIONS

Correia et al., "High-Selectivity Single-Chip Spectrometer in Silicon for Operation at Visible Part of the Spectrum",☐☐IEEE Transactions on Electron Device, vol. 47, No. 3, Mar. 2000.*
Hinnrichs, Michele, "Hand Held Imaging Spectrometer", Proceedings of the 31st Applied Imagery Pattern Recognition Workshop (2002), pp. 1-7.*
U.S. Appl. No. 11/016,952, filed Dec. 20, 2004, Mestha et al.

* cited by examiner

*Primary Examiner*—Tarifur R. Chowdhury
*Assistant Examiner*—Jonathan M Hansen
(74) *Attorney, Agent, or Firm*—Oliff & Berridge, PLC

(57) ABSTRACT

A low cost spectral camera may include a multiple Fabry-Perot cavity filter with silicon photodetectors distributed one beside another in a two-dimensional matrix fashion. Each cavity may be designed to capture a pixel from an image. The two-dimensional fabry-perot array may function as a sensor to capture an image in spectral form. Spectral information may be obtained to generate spectral displays.

17 Claims, 6 Drawing Sheets

TWO-DIMENSIONAL SPECTRAL CAMERAS AND METHODS FOR CAPTURING SPECTRAL INFORMATION USING TWO-DIMENSIONAL SPECTRAL CAMERAS

Cross-reference is made to co-pending, commonly assigned application, U.S. application Ser. No. 11/016,952, filed Dec. 20, 2004, by Mestha et al., entitled "Full Width Array Mechanically Tunable Spectral Spectrophotometer," and U.S. Pat. No. 6,295,130 issued Sep. 25, 2001, the entire disclosures of which are herein incorporated by reference.

BACKGROUND

Digital cameras are a fast-growing segment of the digital consumer market, and are used largely for producing photographic images. Each pixel of a subject is captured digitally in terms of RGB (red, green and blue) separations. Currently, low cost, higher mega pixel digital still and video cameras are entering consumer market.

Digital cameras typically use charged-couple-device (CCD) or complementary metal-oxide semiconductor (CMOS) chips as image sensors. Such CCD or CMOS chips record light from a subject when capturing an image of the subject.

SUMMARY

The above-discussed digital cameras are mainly point-and-shoot cameras which give relatively low-resolution color images. RGB data obtained from such low-resolution cameras give significant color distortions. Thus, such low-resolution digital cameras are not suitable for certain applications, such as non-invasive diagnosis, for example, for diagnosing and monitoring infections, accurate human identifications from color images, provision of human-like computer vision to robots, remote sensing or the like.

Various exemplary systems and methods provide low cost spectral cameras, such as two-dimensional spectral cameras, that include a plurality of spectrophotometers, for example, in a two-dimensional array, such as a multiple Fabry-Perot cavity filter with silicon photo-detectors distributed one beside another in a two-dimensional matrix fashion. Each cavity may be designed to capture a pixel from an image. Such spectral cameras may use, for example, Fabry-Perot type two-dimensional spectral sensors in place of CCD/CMOS RGB chips found in conventional digital cameras. A two-dimensional Fabry-Perot MEMS (micro-electro-mechanical-system) array may function as an image sensor to capture the image in spectral form. The captured spectral image data may be displayed as a conventional image, or as a plurality of spectral images. The image data may also be output to an external device for display or further processing.

These and other features and details are described in, or are apparent from, the following detailed description.

BRIEF DESCRIPTION OF THE DRAWINGS

Various exemplary details of systems and methods are described, with reference to the following figures, wherein.

DETAILED DESCRIPTION OF EMBODIMENTS

The basic structure of a Fabry-Perot cavity spectrophotometer is described in detail in U.S. Pat. No. 6,295,130, which is incorporated herein by reference in its entirety. The basic Fabry-Perot spectrophotometer includes two micro-mirrors separated by a gap. The gap may be an air gap, or may be filled with liquid or other material. The micro-mirrors include multi-layer distributed Bragg reflector (DBR) stacks or highly reflective metallic layers, such as gold. A voltage applied between the two mirrors may be adjusted to change a dimension of the gap, such as a size of the gap. The size of the gap may also be called a width or height of the gap. Only light with certain wavelength may be able to pass the gap due to interference effect of incident light and reflective light.

Figure 1:
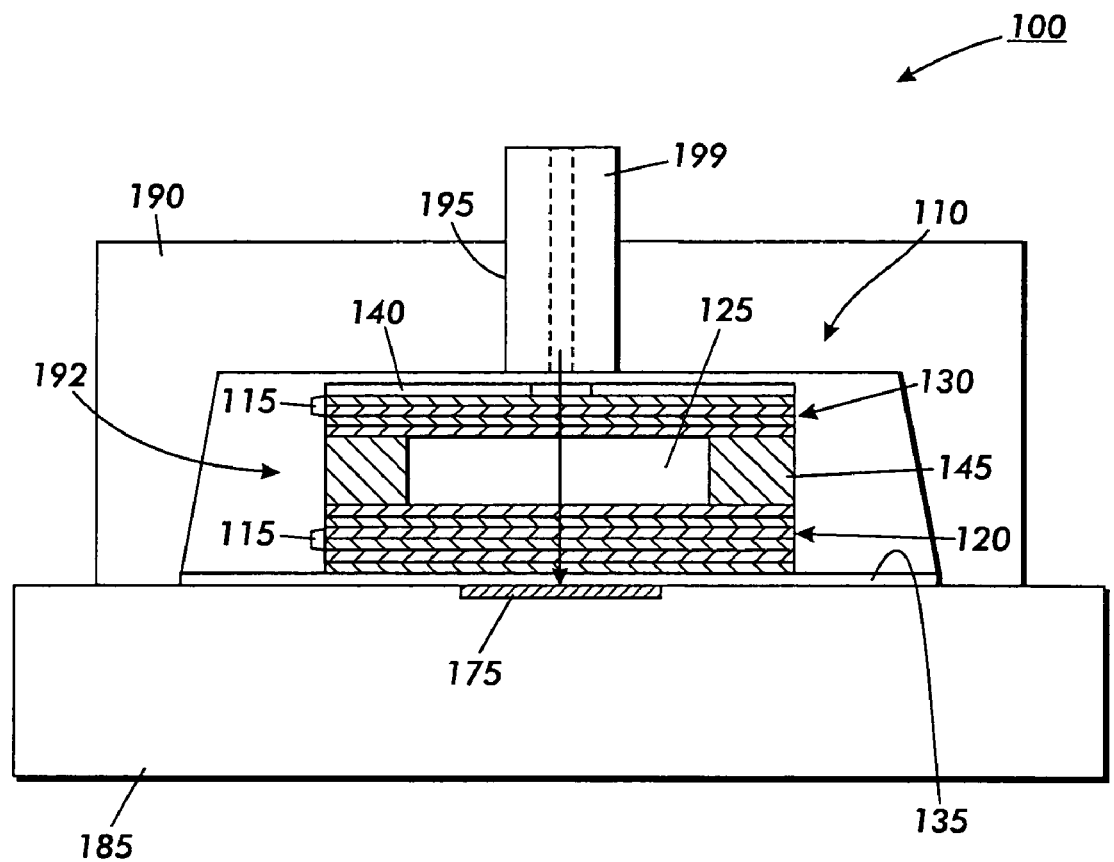
FIG. 1 illustrates an exemplary Fabry-Perot spectrophotometer.

For example, FIG. 1 shows an embodiment of a micro-electro-mechanically tunable spectrophotometer. As described in the 130 patent, a Fabry-Perot cavity filter 110 includes three pairs of quarter wavelength $Si/SiN_x$ stacks 115 for a bottom distributed Bragg reflector (DBR) mirror 120, a gap cavity 125 and two pairs of quarter wavelength $Si/SiN_x$ stacks 115 for a top distributed Bragg reflector (DBR) mirror 130. Indium tin oxide (ITO) may be used for a transparent bottom electrode 135 and a transparent top electrode 140.

Top mirror 130 may be deformed to a dimensional change in the gap cavity 125 by applying a voltage in the range of 100 volts across transparent bottom electrode 135 and transparent top electrode 140, or a charge in the range of $10^{-11}$ coulombs on transparent bottom electrode 135 and transparent top electrode 140 to effect a change in the dimension, such as the size, of gap cavity 125 of about 300 to 500 nm. Hence, electrodes 135 and 140 may form a capacitor and Fabry-Perot cavity filter 110 may have an associated capacitance. As the size of gap cavity 125 decreases, the Fabry-Perot transmission peak shifts to shorter wavelengths, as shown in FIGS. 2 and 3, where gap cavity 125 size decreases to the left.

For example, for gap cavity 125 having a size of 750 nm, quarter wavelength $Si/SiN_x$ stacks 115 have a central wavelength of 700 nm. As the size of gap cavity 125 is decreased, shorter wavelength spectral peaks are resolved by photodetector 175. Typical response time for photodetector 175 is about $10^{-10}$ seconds, whereas mechanical response times typically are on the order of $10^{-6}$ seconds.

Figure 2:
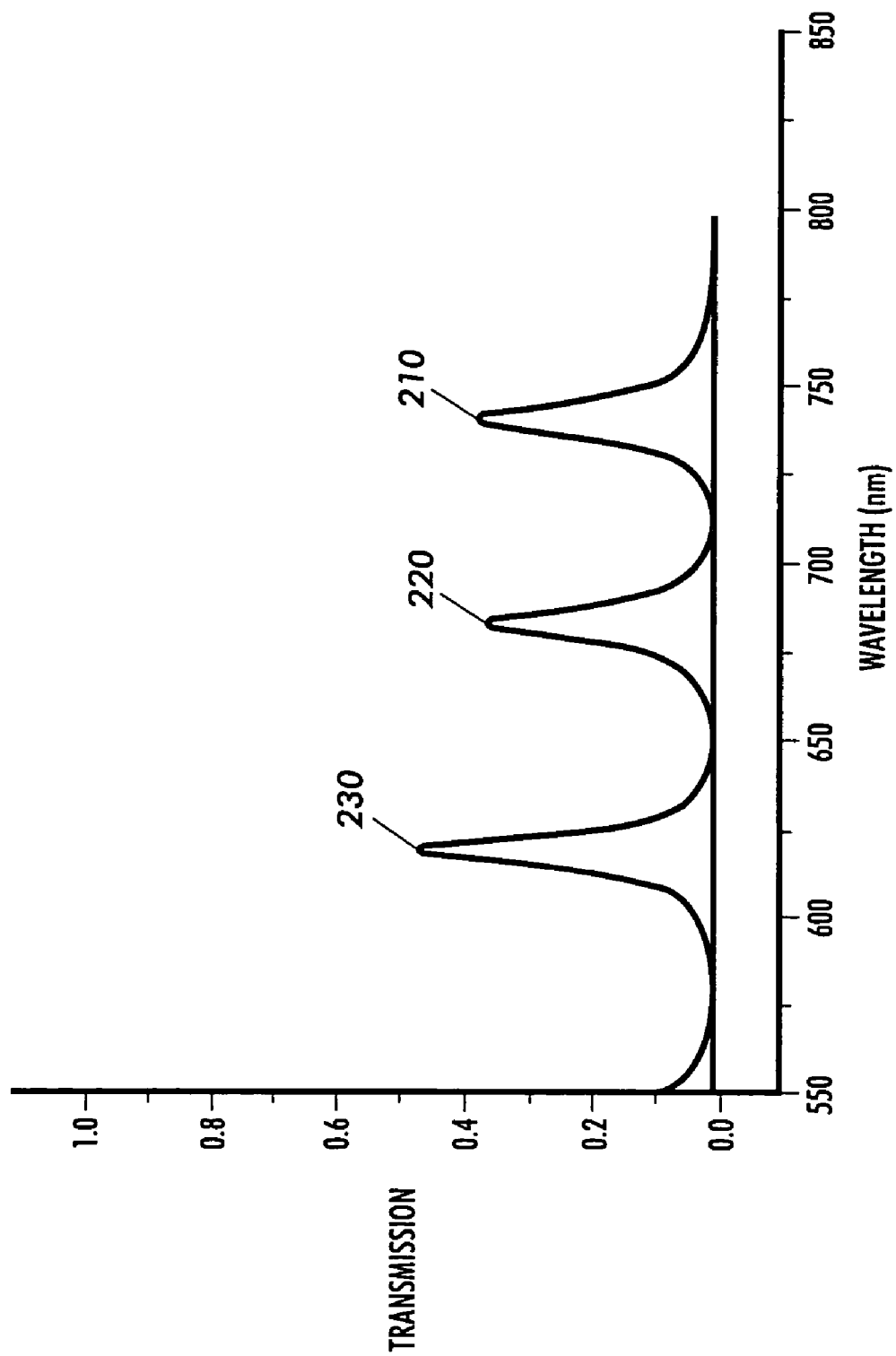
FIGS. 2 and 3 illustrate the dependence of light transmission on wavelength with decreasing gap size in the Fabry-Perot spectrophotometer shown in FIG. 1.
Figure 3:
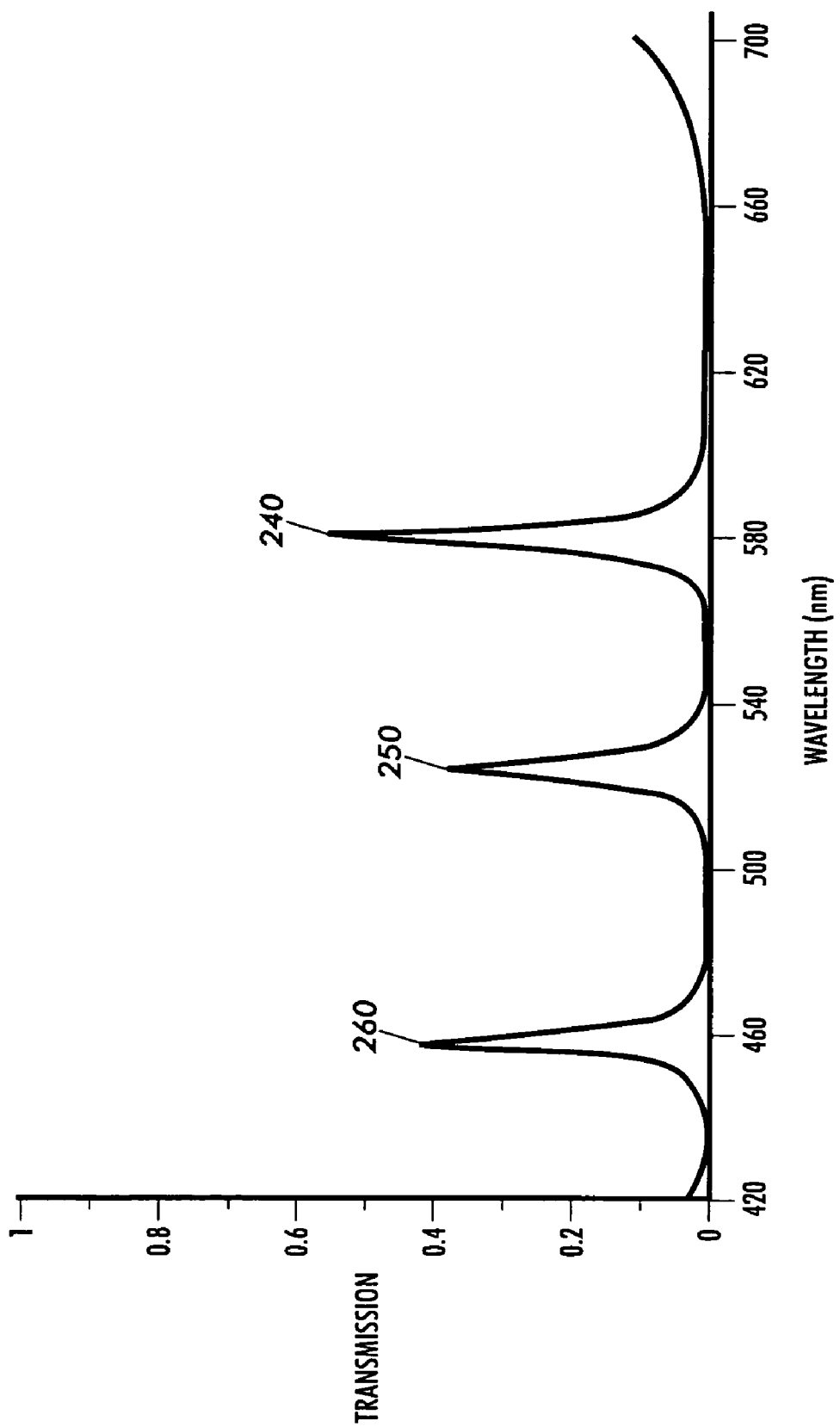

The transmission wavelength tuning of Fabry-Perot cavity filter 110 is simulated in FIGS. 2 and 3. Fabry-Perot cavity filter 110 in FIG. 2 uses quarter wavelength $Si/SiN_x$ stacks 115 centered at 700 nm. The tunable range for quarter wavelength $Si/SiN_x$ stacks 115 centered at 700 nm stops at 600 nm. Fabry-Perot cavity filter 110 in FIG. 3 uses quarter wavelength $Si/SiN_x$ stacks 115 centered at 500 nm. The tunable range for quarter wavelength $Si/SiN_x$ stacks 115 centered at 500 nm is limited to 450 nm for the lower end of the range. Hence, using two Fabry-Perot cavity filters 110, for example, with first Fabry-Perot cavity filter 110 being centered at 700 nm and second being Fabry-Perot cavity filter 110 centered at 500 nm, allows coverage of the entire visible spectrum.

By calculating the transmission of Fabry-Perot cavity filter 110 with quarter wavelength $Si/SiN_x$ stacks 115 centered at 700 nm (see FIG. 2) and Fabry-Perot cavity filter 110 with quarter wavelength Si/SiN$_x$ stacks 115 centered at 500 nm (see FIG. 3) as a function of wavelength for gap cavity 125 with peak 210 at approximately 740 nm, peak 220 at approximately 680 nm, peak 230 at approximately 620 nm and peak 240 at approximately 580 nm, peak 250 at approximately 530 nm, peak 260 at approximately 460 nm, respectively, the transmission spectrum for both Fabry-Perot cavity filters 110 may be determined as a function of bias voltage. To avoid intensity contributions below 600 nm when using Fabry-Perot cavity filter 110 with quarter wavelength Si/SiN$_x$ stacks 115 centered at 700 nm, a color filter may be used to prevent wavelengths below 600 nm from reaching photodetector 175. The color filter may be needed because wavelengths shorter than 600 nm are transmitted through Fabry-Perot cavity filter 110 with quarter wavelength Si/SiN$_x$ stacks 115 centered at 700 nm.

When microelectromechanically tunable spectrophotometer 100 is calibrated with a calibration light source, the bias voltage needed to tune Fabry-Perot filter 110 to a certain wavelength is known. Therefore, two microelectromechanically tunable spectrophotometers 100 enable the output of spectral intensity as a function of wavelength for the entire visible spectrum. The co-pending application "Full Width Array Mechanically Tunable Spectral Spectrophotometer" (Ser. No. 11/016,952) discloses such calibration systems and methods. In embodiments of the co-pending application, a full width array document scanning spectrophotometer (FWAS) integrates a Fabry-Perot cavity filter with a silicon photodetector and a light focusing device, such as an optical fiber or a SELFOC® lens. An item or material, such as a print document to be scanned for calibrating and ultimately maintaining color accuracy, may be illuminated by a two-sided LED illuminator bar, wherein the illuminator bar may be advantageously comprised of white LEDs or a fluorescence light source. The thickness of the cavity filter may be tuned electrostatically with a switching circuit to give multiple transmissive frequency measurements to the photodetector and a sampling circuit for resolving the spectral distribution of the transmitted light signal from the object media. The architecture of the full width array spectrophotometer may facilitate representative spectral detection without the need for plural different color light source emissions, thereby engendering multiple illuminate reflections from a single light source on a target media to produce multiple samples. Thus, multiple samples may be derived from a single illuminate source by corresponding adjustment by the optical filter with enough samples to define a characterizing spectral response. A spectral reconstruction technique may facilitate the resolving of the spectral distribution in the presence of multiple resonant peaks transmitted by the filter.

More particularly, in exemplary embodiments of the co-pending application, an elongated array of multiple, closely spaced photodetectors may be disposed adjacent the illumination source, wherein the spectrophotometers may be positioned to receive light reflected from the target sample. The switching circuit may selectively ramp a voltage source to the optical filter for microelectronically tuning the cavity filter and selectively transmitting therethrough the desired frequencies of reflected light which may be sampled by the sampling circuit for generating the desired representative spectral responses of the target sample.

In the co-pending application, exemplary methods are described for full width scanning color analysis of transversely extensive color test targets in a test target path, such as a color printer path, with a full width array spectrophotometer. A substantially linear elongated array of closely spaced multiple LED illumination sources may be illuminated for illuminating a transversely substantial span of the test target with an illuminated band extending transversely across the test target. Reflected light from the illuminated band may be detected with a full width array of multiple, closely spaced plural photodetectors disposed adjacent to and extending substantially parallel to the array of illumination sources. The photodetectors may be positioned to receive light reflected from the illuminated band fully across the test target. The reflected light may be selectively filtered with the full width array of tunable optical filters associated with the photodetectors for generating a detected spectra from the test targets representative of a color thereof.

The optical filters may preferably comprise microelectronically tunable Fabry-Perot optical filters which may be adjusted by a switching circuit for transmitting selected frequencies of the reflected light from the test target to the photodetectors.

Exemplary systems and methods disclosed in the co-pending application may be operated and controlled by appropriate operation of conventional control systems. It is well known and may be preferable to program and execute such control functions and logic with software instructions for conventional or general purpose microprocessors, as taught by numerous prior patents and commercial products. Such programming or software may of course vary depending on the particular functions, software type, and microprocessor or other computer system utilized, but will be available to, or readily programmable without undue experimentation from, functional descriptions, such as those provided herein, in the cited prior patents and applications herein, and/or prior knowledge of functions which are conventional, together with general knowledge in the software or computer arts. Alternatively, exemplary control systems or methods may be implemented partially or fully in hardware, using standard logic circuits or single chip VLSI designs.

Spectral resolution of spectrophotometer 100 depends on the mean reflectivity of top mirror 130 and bottom mirror 120; higher mean reflectivity provides higher spectral resolution. For spectrophotometer 100, a spectral resolution of 10 nm is typical for color printing applications. The spectral range that Fabry-Perot cavity filter 110 may resolve depends on the initial size of gap cavity 125 and quarter wavelength Si/SiN$_x$ stacks 115 that are used. For light in the infrared regime, the size of gap cavity 125 may be on the order of the infrared wavelength range. The mechanical tuning range of top mirror 130 may be structurally limited, further limiting the spectral range for Fabry-Perot cavity filter 110. If the mechanical tuning range of the mirror 130 is too small, or the spectral range resulting from the gap cavity 125 and the quarter wavelength Si/SiN$_x$ stacks 115 is too narrow for a particular application, a system consisting of more than one spectrophotometers 100 with different initial size of gap cavity 125 and different quarter wavelength stack 115 may be used to cover the spectral range required. More than one spectrophotometers 100 may be used for a system to cover the spectrum from ultra-violet (UV) to infrared (IR).

Figure 4:
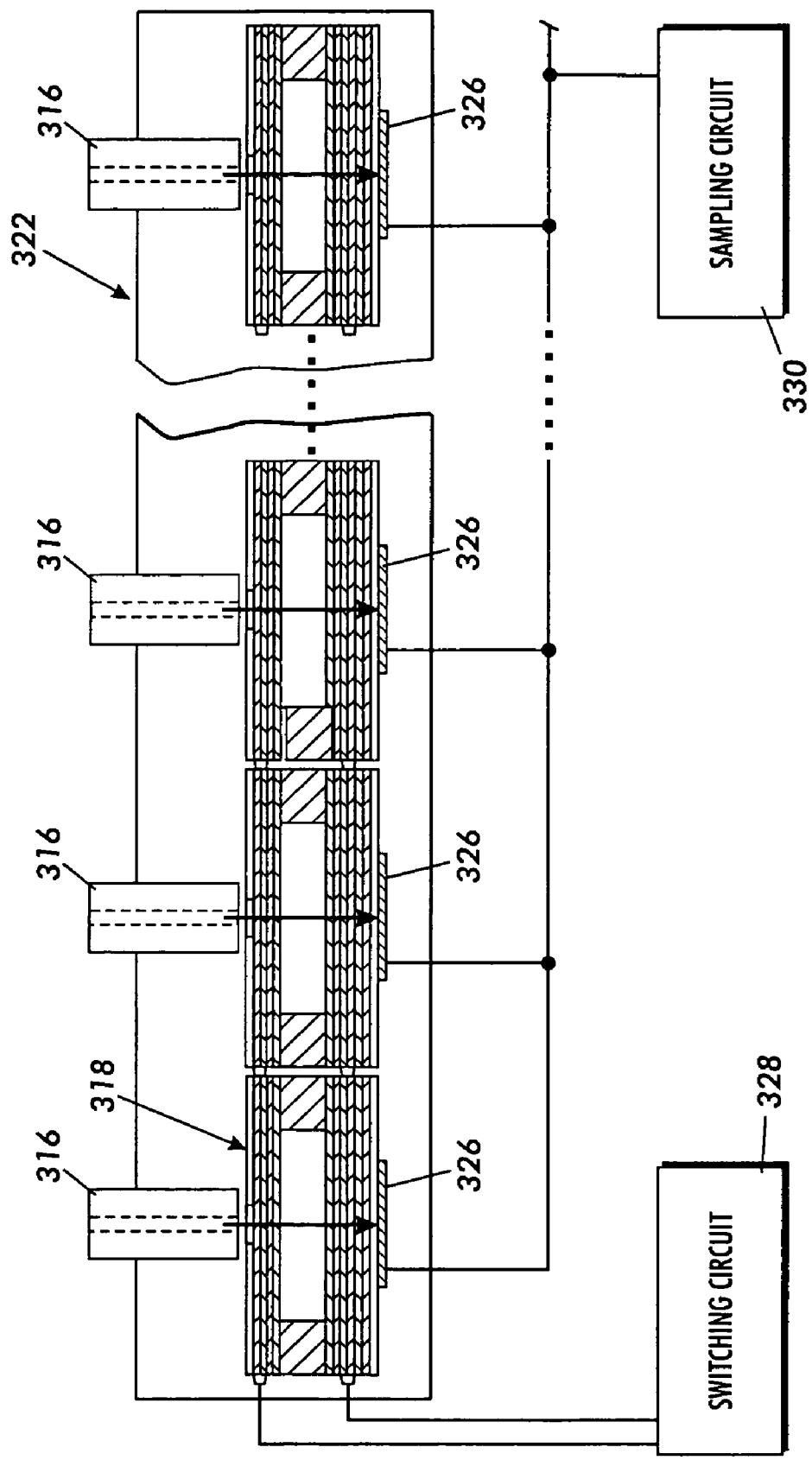
FIG. 4 shows an elevated side view of an exemplary two-dimensional Fabry-Perot cavity array in combination with schematic representations of associated exemplary control systems.

FIG. 4 illustrates an exemplary arrayed assembly architecture of a linear MEMS full width array sensor assembly 322. Reflected light from a document (not shown) is communicated through a light focusing device assembly 316 through an optical filter 318 to a plurality of photodetectors 326. For example, the light focusing device assembly 316 may be an optical fiber. The Fabry-Perot cavity thickness may be tuned electrostatically by a switching circuit 328 to get multiple measurements to resolve the spectral distribution of the transmitted light signal. The gap size of the cavity in the filter may be related to the tunable voltage from the switching circuit 328, and may provide either a single or multiple peak of transmitted frequency of the reflected light.

In FIG. 4, before reaching the Fabry-Perot two-dimensional array sensor assembly 322, the incident light may pass through a lens assembly in a standard digital camera setting. As shown in FIG. 4, the Fabry-Perot two-dimensional array version of the sensor assembly 322 may provide spectral information for each pixel of the incident image. For example, the thickness of the cavity filter may be tuned electrostatically with the switching circuit 328 to give multiple transmissive frequency measurements to the photodetector and a sampling circuit 330 for resolving the spectral distribution of the transmitted light signal from the object media. For example, as described above with respect to the incorporate co-pending application, the architecture of the full width array spectrophotometer may facilitate representative spectral detection without the need for plural different color light source emissions, thereby engendering multiple illuminate reflections from a single light source on a target media to produce multiple samples. Thus, multiple samples may be derived from a single illuminate source by corresponding adjustment by the optical filter with enough samples to define a characterizing spectral response. A spectral reconstruction technique may facilitate the resolving of the spectral distribution in the presence of multiple resonant peaks transmitted by the filter.

As discussed above, the spectral information may be digitally sampled by the sampling circuit 330, for example, using a typical timing generator. For example, the size of the gap may be changed to correspond to different wavelengths, so that spectral information may be obtained. Thus, when the size of the gap is adjusted, the spectral information may subsequently be converted to a digital signal by the sampling circuit 330. The digital signal may be further processed for appropriate applications.

Figure 5:
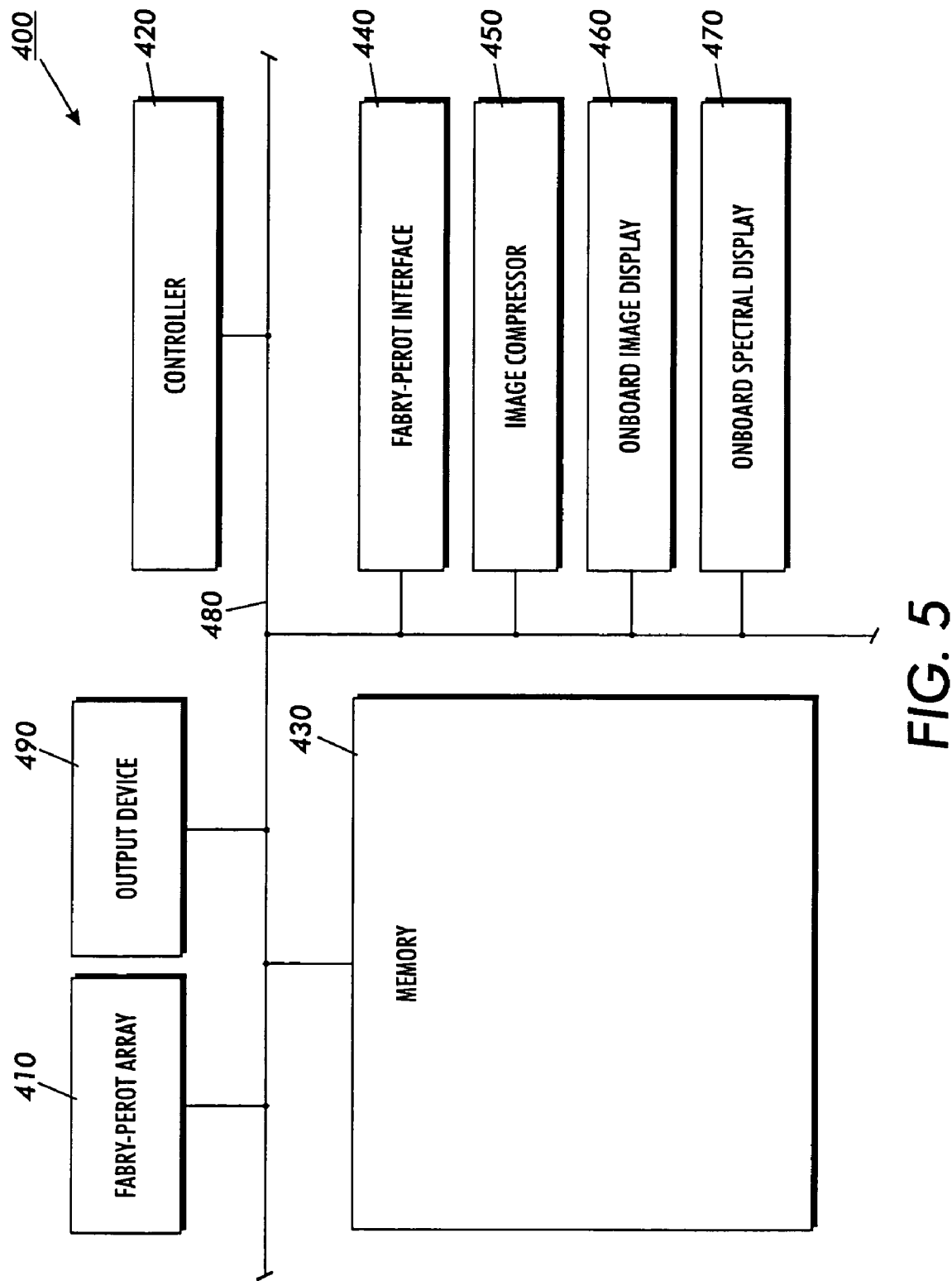
FIG. 5 is a block diagram illustrating an exemplary spectral camera.

FIG. 5 illustrates a block diagram of an exemplary spectral camera 400. The spectral camera 400 may be a two-dimensional spectral camera. As shown in FIG. 5, the spectral camera 400 may include a Fabry-Perot two-dimensional array 410, a controller 420, a memory 430, a Fabry-Perot interface 440, an image processor, such as an image compressor 450, an image display 460, a spectral display 470 and an output device 490, each connected by connection or bus 480. Each of the image display 460 and the spectral display 470 may be onboard, integrated with or detachably connected to the spectral camera 400.

The Fabry-Perot two-dimensional array 410 may be a device similar to the Fabry-Perot array 322 described above in connection with FIG. 4. For example, an incident image may pass through a lens and arrive at the Fabry-Perot two-dimensional array 410. The Fabry-Perot two-dimensional array 410 may include a switching circuit to change the size of a gap. The Fabry-Perot two-dimensional array 410 may also include a sampling circuit and processing algorithms that obtains spectral images or spectral contents from the incident image. Such spectral image or spectral contents may include hyperspectral images. The sampled spectral information may be converted to a digital signal.

As shown in FIG. 5, the controller 420 may control a lens positioned before the Fabry-Perot two-dimensional array 410 to adjust the incident light, the switching circuit to change the size of a gap, and the sampling circuit and processing algorithms to obtain spectral contents from the incident image. The controller 420 may also control the image compressor 450, the image display 460, and the spectral display 470 to perform their various functions.

The controller 420 may provide the digitized spectral information to other electronics drivers, such as a gain controller, an amplifier or the like (not shown) via the Fabry-Perot interface 440. Such electronics drivers may be used, for example, to improve the signal-to-noise (S/N) ratio of the digitized spectral information.

The image compressor 450, under control of the controller 420, may spectrally synthesize the digitized spectral information for display as a composite image. The image compressor 450 may also compress the digitized spectral information to be output for subsequent processing, synthesis or display. The image display 460 may be used to display the image, if desired, which is a synthesized image having all or selected spectral information. On the other hand, the spectral display 470 may display, if desired, spectral information of the image. For example, a spectral image may be displayed based on the spectral information obtained at a single wavelength. The image display 460 and the spectral display 470 may display image or spectral information for a selected area of the image.

The spectral information and the image may be exported, via the output device 490, to an external device, such as a personal computer (PC) or a television, for display or for further analysis. The memory 430 may be used to store image information and spectral information produced in various stages of an image capturing process using the spectral camera 400. The connection 480 may be a data bus, an application interface, or any wired or wireless connection.

Figure 6:
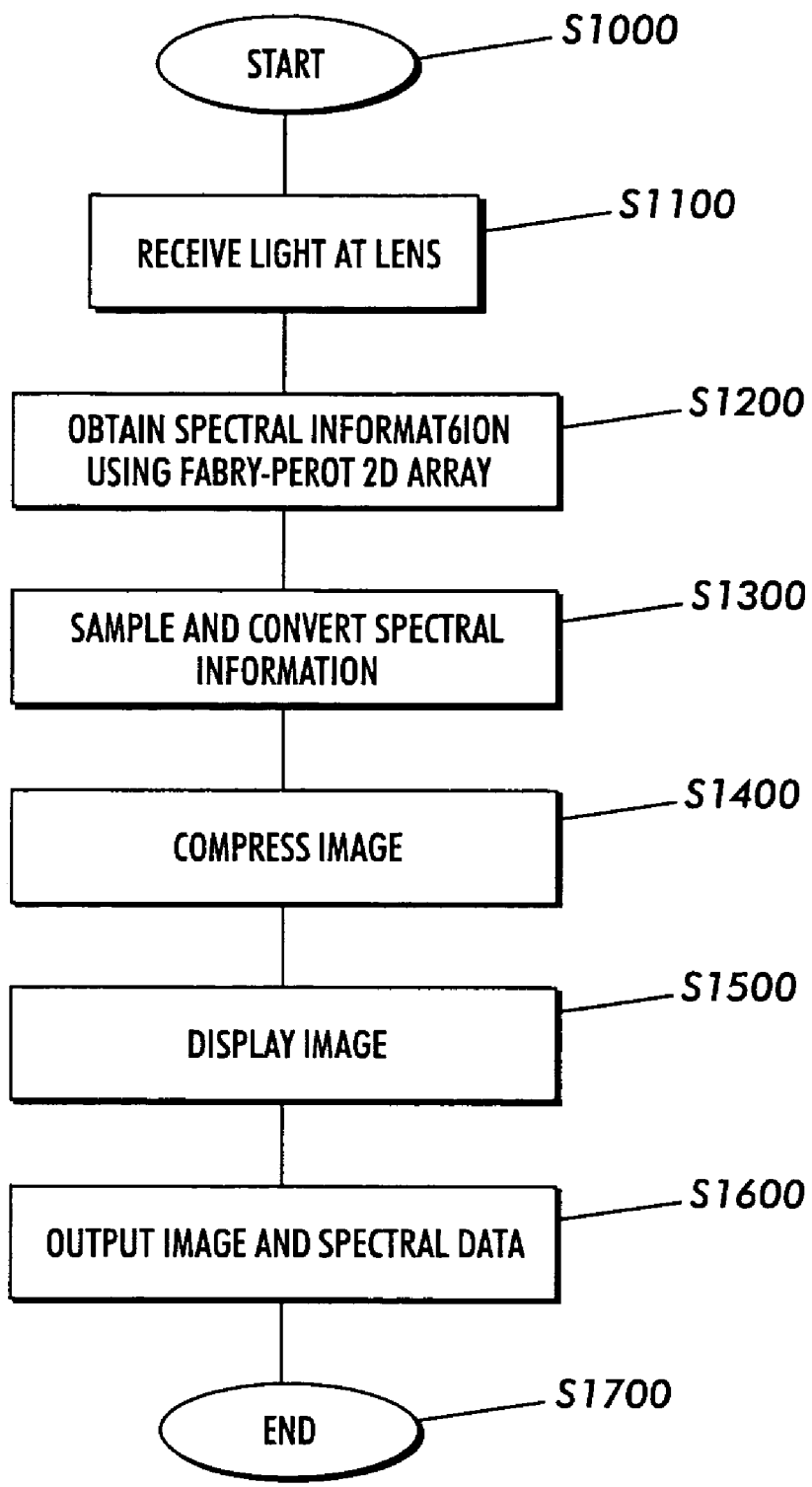
FIG. 6 outlines an exemplary process for capturing an image using a spectral camera.

FIG. 6 outlines an exemplary image capturing process using a spectral camera. As shown in FIG. 6, starting from step S1000, the process proceeds to step S1100, where the spectral camera receives at a lens incident light which may have been reflected from an object or a target. Next, in step S1200, the spectral camera obtains spectral information of the incident light using a Fabry-Perot two-dimensional array by adjusting the size of gap between the pair of mirrors in a Fabry-Perot cavity. Process then proceeds to step S1300.

In step S1300, the spectral camera samples the spectral information, and converts the sampled spectral information into digital data appropriate for, for example, intended applications. Next, in step S1400, the digitized spectral information may be compressed to be output for subsequent processing, synthesis or display at an external device. The digitized spectral information may also be synthesized for display. The process then proceeds to step S1500.

In step S1500, the image or spectral information is displayed at a display the spectral camera, if desired. The display may be an image display in which all spectral information or spectral information selected at two or more wavelengths are displayed. Alternatively, the display may be one or more spectral displays, with each spectral display displaying only spectral information of a single wavelength. The display may be for a selected area of the image or may be for the whole image.

Next, in step S1600, the image and spectral data is output, if desired, to an external device for display or for further analysis. Thereafter, process proceeds to step S1700, where the process ends.

The method illustrated in FIG. 6 may be implemented in a computer program product that may be executed on a computer. The computer program product may be a computer-readable recording medium on which a control program is recorded, or may be a transmittable carrier wave in which the control program is embodied as a data signal.

It should be noted that, by selecting proper design of the gap, the spectral camera may be used as a conventional RGB imager, without foregoing the advantages of the conventional digital cameras.

The spectral camera may be used in a plurality of applications. For example, the spectral camera may be used in a device for home medical diagnosis, such as home mammographic and tissue disease diagnosis; and for food quality determination, such determination of water content and other ingredients in a dairy produce. To perform these functions, it may be necessary to customize post-processing software that is to be included in a spectral camera tailored to a specific need. The spectral images obtained from the spectral camera will retain photo-realistic and lively images electronically. For example, doctors may use the spectral images potentially for remote diagnosis at a later time.

By using Fabry-Perot spectral photometers, the digital camera may be manufactured with low cost. Thus, the spectral camera may be easily integrated into various process monitoring and other related real-time rapid feedback control applications. For example, the spectral camera may be integrated into a device used for packaging, monitoring and controlling drugs in manufacturing lines. Such applications improve drug product quality and consistency. Also, such a device may be used to test medicine tablets without destroying the tablets, thus eliminating destructive warehouse tests.

In addition, the spectral camera may be used for security applications, such as identification of humans. For example, using a human identification algorithm in an embedded software module inside an MEMS spectral camera, identification of images and faces may be made accurately. Similar application may exist in skin imagery for cosmetics and dental analysis.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art which are also intended to be encompassed by the following claims.

What is claimed is:

1. A two-dimensional spectral camera, comprising:
a plurality of spectrophotometers, each comprising a Fabry-Perot cavity that includes a pair of Bragg reflectors with a gap between each pair of Bragg reflectors, each cavity designed to capture a pixel from an image, the plurality of spectrophotometers comprising (1) at least one two-dimensional array of spectrophotometers having only Fabry-Perot cavities with an initial size of gap cavity on the order of an ultra-violet wavelength range, (2) at least one two-dimensional array of spectrophotometers having only Fabry-Perot cavities with an initial size of gap cavity on the order of a visible light wavelength range, and (3) at least one two-dimensional array of spectrophotometers having only Fabry-Perot cavities with an initial size of gap cavity on the order of an infrared wavelength range;
a light focusing device that focuses incident light;
a controller;
a sampling circuit; and
a compressor that compresses digital data and outputs compressed digital data to an external device,
wherein the image comprises incident light reflected from a target, and
wherein the controller controls the sampling circuit to sample spectral information from the received light to generate spectral image data, and to convert the sampled spectral information into the digital data.

2. The spectral camera of claim 1, further comprising a spectral display that displays at least one spectral image based on the digital data, the at least one spectral image containing information associated with at least a single wavelength.

3. The spectral camera of claim 1, further comprising:
a processor; and
an image display,
wherein the processor spectrally synthesizes the digital data to generate a spectral image that contains information associated with at least two wavelengths, and the image display displays the generated spectral image.

4. The spectral camera of claim 1, wherein the controller controls the sampling circuit to convert the sampled spectral information into a spectra.

5. An apparatus for obtaining spectral data, comprising:
the spectral camera according to claim 1; and
a processor that processes the sampled spectral information from the spectral camera.

6. The spectral camera of claim 1, the light focusing device being an optical fiber.

7. The spectral camera of claim 1, wherein said plurality of spectrophotometers comprises at least two two-dimensional arrays of spectrophotometers having only Fabry-Perot cavities with an initial size of gap cavity on the order of a visible light wavelength range.

8. A method of capturing spectral data using a two-dimensional spectral camera, the spectral camera including a plurality of spectrophotometers and a sampling circuit, the method comprising:
receiving incident light reflected from a target using the plurality of spectrophotometers, each comprising a Fabry-Perot cavity that includes a pair of Bragg reflectors with a gap between each pair of Bragg reflectors, each cavity designed to capture a pixel from an image comprising the incident light, the plurality of spectrophotometers comprising (1) at least one two-dimensional array of spectrophotometers having only Fabry-Perot cavities with an initial size of gap cavity on the order of an ultra-violet wavelength range, (2) at least one two-dimensional array of spectrophotometers having only Fabry-Perot cavities with an initial size of gap cavity on the order of a visible light wavelength range, and (3) at least one two-dimensional array of spectrophotometers having only Fabry-Perot cavities with an initial size of gap cavity on the order of an infrared wavelength range;
focusing the incident light by a light focusing device;
sampling spectral information from the received light using the sampling circuit;
generating spectral image data based on the sampled spectral information;
converting the sampled spectral information into digital data;
compressing the digital data; and
outputting the compressed digital data to an external device.

9. The method of claim 8, further comprising displaying at least one spectral image based on the digital data, the at least one spectral image containing information associated with at least a single wavelength.

10. The method of claim 8, further comprising:
spectrally synthesizing the digital data to generate a spectral image that contains information associated with at least two wavelengths; and
displaying the generated spectral image.

11. The method of claim 8, wherein the spectral camera includes a lens, the method further comprising:
- receiving incident light via the lens; and
- passing the incident light from the lens to the plurality of spectrophotometers.

12. The method of claim 8, further comprising:
converting the sampled spectral information into a spectra.

13. The method of claim 8, the light focusing device being an optical fiber.

14. The method of claim 8, wherein the plurality of spectrophotometers comprises at least two two-dimensional arrays of spectrophotometers having only Fabry-Perot cavities with an initial size of gap cavity on the order of a visible light wavelength range.

15. A computer-readable medium including computer-executable instructions embedded thereon for capturing spectral data using a two-dimensional spectral camera, the spectral camera including a plurality of spectrophotometers and a sampling circuit, the instructions comprising:
- instructions for receiving incident light reflected from a from an outside target using the plurality of spectrophotometers, each comprising a Fabry-Perot cavity that includes a pair of Bragg reflectors with a gap between each pair of Bragg reflectors, each cavity designed to capture a pixel from an image comprising the incident light, the plurality of spectrophotometers comprising (1) at least one two-dimensional array of spectrophotometers having only Fabry-Perot cavities with an initial size of gap cavity on the order of an ultra-violet wavelength range, (2) at least one two-dimensional array of spectrophotometers having only Fabry-Perot cavities with an initial size of gap cavity on the order of a visible light wavelength range, and (3) at least one two-dimensional array of spectrophotometers having only Fabry-Perot cavities with an initial size of gap cavity on the order of an infrared wavelength range;
- instructions for focusing the incident light by a light focusing device;
- instructions for sampling spectral information from the received light using the sampling circuit;
- instructions for generating spectral image data of the target based on the sampled spectral information;
- instructions for converting the sampled spectral information into digital data;
- instructions for compressing the digital data; and
- instructions for outputting the compressed digital data to an external device.

16. The computer-readable medium of claim 15, the light focusing device being an optical fiber.

17. The computer-readable medium of claim 15, wherein the plurality of spectrophotometers comprises at least two two-dimensional arrays of spectrophotometers having only Fabry-Perot cavities with an initial size of gap cavity on the order of a visible light wavelength range.

* * * * *